(12) United States Patent
Zhang et al.

(10) Patent No.: US 12,092,601 B2
(45) Date of Patent: Sep. 17, 2024

(54) CONSTRUCTION METHOD FOR PHOTOCATHODE INDIRECT COMPETITION SENSOR AND EVALUATION METHOD

(71) Applicants: Oil Crops Research Institute of Chinese Academy of Agricultural Sciences, Wuhan (CN); Wuhan Norrida Biotechnological Co., LTD, Wuhan (CN)

(72) Inventors: Zhaowei Zhang, Wuhan (CN); Wenqin Wu, Wuhan (CN); Xiao Chen, Wuhan (CN); Ling Cheng, Wuhan (CN); Li Yu, Wuhan (CN); Xiupin Wang, Wuhan (CN); Peiwu Li, Wuhan (CN)

(73) Assignees: Oil Crops Research Institute of Chinese Academy of Agricultural Sciences, Wuhan (CN); Wuhan Norrida Biotechnological Co., LTD, Wuhan (CN)

( * ) Notice: Subject to any disclaimer, the term of this patent is extended or adjusted under 35 U.S.C. 154(b) by 0 days.

(21) Appl. No.: 18/342,808

(22) Filed: Jun. 28, 2023

(65) Prior Publication Data
US 2023/0341346 A1 Oct. 26, 2023

(30) Foreign Application Priority Data
Jun. 29, 2022 (CN) .................. 202210747865.9

(51) Int. Cl.
| | |
|---|---|
| *G01N 27/30* | (2006.01) |
| *G01N 21/31* | (2006.01) |
| *G01N 23/20* | (2018.01) |
| *G01N 23/20091* | (2018.01) |
| *G01N 23/2251* | (2018.01) |
| *G01N 24/00* | (2006.01) |
| *G01N 27/27* | (2006.01) |
| *G01N 27/327* | (2006.01) |
| *G01N 33/569* | (2006.01) |

(52) U.S. Cl.
CPC .......... *G01N 27/305* (2013.01); *G01N 21/31* (2013.01); *G01N 23/20* (2013.01); *G01N 23/20091* (2013.01); *G01N 23/2251* (2013.01); *G01N 24/00* (2013.01); *G01N 27/27* (2013.01); *G01N 27/3275* (2013.01); *G01N 33/56961* (2013.01); *G01N 2333/38* (2013.01)

(58) Field of Classification Search
CPC .. G01N 27/305; G01N 27/27; G01N 27/3275; G01N 21/31; G01N 23/20; G01N 23/20091; G01N 23/2251; G01N 24/00
See application file for complete search history.

(56) References Cited

U.S. PATENT DOCUMENTS

| | | | |
|---|---|---|---|
| 2012/0205518 A1 | 8/2012 | Voutilainen et al. | |
| 2014/0145065 A1 | 5/2014 | Uozumi et al. | |
| 2015/0102205 A1 | 4/2015 | Baba et al. | |
| 2023/0168184 A1* | 6/2023 | Maale | G01N 21/211 |
| | | | 435/6.12 |

FOREIGN PATENT DOCUMENTS

CN 116148322 A * 8/2023 ............. G01N 27/26

OTHER PUBLICATIONS

Chen et al. "Z-scheme Bi2O3/CuBi2O4 heterjunction enabled sensitive photoelectrochemical detection of aflatoxin B1 for health care, the environment, and food", Biosensors and Bioelectronics, 214, 2022, 114523. Published online Jun. 20, 2022. (Year: 2022).*
Hou et al. "Construction of a double Z-scheme Bi2O3—CuBi2O4—CuO composite photocatalyst for the enhanced photocatalytic activity", Ceramics International, 48, 2022, 20648-20657. published online Apr. 11, 2022. (Year: 2022).*
Majhi et al. "Plasmonic Ag nanoparticle decorated Bi2O3/CuBi2O4 photocatalyst for expeditious degradation of 17a-ethinylestradiol and Cr(VI) reduction: insight into electron transfer mechanism and enhanced photocatalytic activity", Chemical Engineering Journal, 413, 2021, 127506. Pub'd Oct. 31, 2020. (Year: 2020).*
Chen et al. "In situ construction of biocompatible Z-scheme a-Bi2O3/CuBi2O4 heterojunction for NO removal under visible light", Applied Catalysis B:Environmental, 272, 2020, 119008. Published online Apr. 18, 2020. (Year: 2020).*
CNIPA, Notification to grant patent right for Chinese application CN202210747865.9, Jun. 1, 2023.

* cited by examiner

*Primary Examiner* — Jane L Stanley
(74) *Attorney, Agent, or Firm* — Zhigang Ma

(57) ABSTRACT

The present disclosure belongs to the technical field of biosensors and particularly provides a construction method for a photocathode indirect competition sensor and an evaluation method. The construction method includes: using Z-type $Bi_2O_3/CuBi_2O_4$ as a sensing platform; calculating a photoinduced electron Z-type transfer path and an energy band structure of $Bi_2O_3$ and $CuBi_2O_4$ using a density functional theory (DFT); and constructing a $Bi_2O_3/CuBi_2O_4$-based biosensor. A photoelectrochemical (PEC) photocathode biosensor based on a $Bi_2O_3/CuBi_2O_4$ heterojunction prepared through the solution has good repeatability, reproducibility, stability, and specificity for detecting a target. The PEC biosensor constructed in the solution of the present disclosure has a broad application prospect in the fields of healthcare, environment, and food.

6 Claims, 2 Drawing Sheets

S1, synthesize $Bi_2O_3/CuBi_2O_4$, $Bi_2O_3$, and $CuBi_2O_4$ using a high-temperature calcination method, uniformly disperse $Bi_2O_3/CuBi_2O_4$ in a dispersion solution by ultrasound, and coat an electrode with droplets, and naturally dry the electrode to obtain a $Bi_2O_3/CuBi_2O_4/ITO$-based sensing platform

S2, perform treatment using a Perdew-Burke-Ernzerhof method with generalized gradient approximation

S3, construct a $Bi_2O_3/CuBi_2O_4$-based sensor

FIG. 1

CONSTRUCTION METHOD FOR PHOTOCATHODE INDIRECT COMPETITION SENSOR AND EVALUATION METHOD

TECHNICAL FIELD

The present disclosure relates to the technical field of biosensors, and more particularly, to a construction method for a photocathode indirect competition sensor and an evaluation method.

BACKGROUND

Photoelectrochemical (PEC) biosensors have the advantages of high sensitivity, simple operation, miniaturization, and low cost, and have been widely used in fields such as healthcare, environmental monitoring, and food safety. Two remaining issues needing to be overcome at present are interference resistance and sensitivity. In order to improve the interference resistance of a photocathode, p-type semiconductor-based photocathode sensors have received increasing attentions. A photocathode sensor can effectively avoid photocorrosion caused by holes on a surface of a photoelectrode and resist interference of reducing substances. In terms of the sensitivity of a PEC sensor, a nanomaterial with high photoelectric activity can improve the separation efficiency and light conversion efficiency of photon-generated carriers. Compared with a wide-band-gap semiconductor ($TiO_2$ 3.2 eV; $WO_3$ 2.7 eV) or a toxic heavy metal (CdS, $CsPbBr_3$), $CuBi_2O_4$, as a promising p-type photocathode material, has the advantages of appropriate optical band gap (1.5-1.8 eV), excellent light resistance and catalytic activity, strong visible light response, and environmental friendliness. Therefore, $CuBi_2O_4$ has received increasing attentions in visible light photocatalytic researches. However, due to the rapid recombination of electron-hole pairs ($e^-/h^+$), the photocatalytic efficiency of pure $CuBi_2O_4$ is relatively low.

In order to improve the photocatalytic performance of $CuBi_2O_4$, various strategies have been explored, including adjusting different forms, doping metal elements, coupling $CuBi_2O_4$ with carbon materials, or constructing heterostructures. Developing heterojunctions using semiconductors such as $TiO_2/CuBi_2O_4$, $CuO/CuBi_2O_4$, $WO_2/CuBi_2O_4$, and $BiOCl/CuBi_2O_4$ can improve the photoelectric activity of the original $CuBi_2O_4$. Due to the following reasons, the heterojunctions contribute to high performance of the PEC biosensors:

Firstly, a suitable heterojunction structure has extremely high visible light absorption capacity, resulting in efficient use of light. Secondly, VB and CB can be appropriately aligned with a band position, to accelerate $e^-/e^+$ migration and reduce charge recombination. A Z-type heterojunction represented by AgI/Ag/BiOI, $In_2O_3/Bi_4O_7$, and CdSe—Ag—$WO_3$—Ag has the advantages of high light trapping capacity and high redox capacity, and has been widely used in detection of chloramphenicol, degradation of antibiotics, and hydrogen evolution reaction. However, there are still problems of low interference resistance, high universality, and insufficient sensitivity. Furthermore, there are few reports using PEC biosensors for indirect competitive immunoassay.

Therefore, constructing a PEC biosensor with good interference resistance and high sensitivity is a major challenge for actual sample detection.

SUMMARY

The present disclosure aims at the technical problems that an existing PEC biosensor has low interference resistance and low sensitivity during actual sample detection in the prior art.

The present disclosure provides a construction method for a photocathode indirect competition sensor, including the following steps:

S1, synthesizing $Bi_2O_3/CuBi_2O_4$, $Bi_2O_3$, and $CuBi_2O_4$ using a high-temperature calcination method, uniformly dispersing $Bi_2O_3/CuBi_2O_4$ in a dispersion solution by ultrasound, and coating an electrode with droplets, and naturally drying the electrode to obtain a $Bi_2O_3/CuBi_2O_4$/ITO-based sensing platform;

S2, performing treatment using a Perdew-Burke-Ernzerhof method with generalized gradient approximation; and S3, constructing a $Bi_2O_3/CuBi_2O_4$-based aflatoxin B1 biosensor.

Preferably, the S1 specifically includes:
grinding and uniformly mixing $Cu(NO_3)_2 \cdot 3H_2O$, $Bi(NO_3)_3 \cdot 5H_2O$, and glucose at a molar ratio of 1:1:7 to 1:5:7 in quartz agate mortar;

drying the mixture at 60° C. for several hours in a ceramic crucible to obtain an anhydrous precursor;

heating the precursor to 400° C., and maintaining the temperature in a tube furnace for 20-40 minutes; and grinding obtained combustion residues in the quartz agate mortar, then calcining same at 500° C. for 2-6 hours in the ceramic crucible, and finally obtaining $Bi_2O_3/CuBi_2O_4$.

Preferably, the S2 specifically includes: for a $Bi_2O_3$ (001)/$CuBi_2O_4$ (100) heterostructure, setting the cut-off energy to be 520 eV;

setting k points for geometric optimization in 2×2×1, and using a 4×4×1 mesh for electronic structure calculation; and setting a vacuum space to be 20 Å to avoid periodic interactions, wherein all structures are loose until the maximum residual force on constituent atoms is less than 0.03 eV/A.

Preferably, the S3 specifically includes:
dripping 5 μL of a glutaraldehyde aqueous solution onto $Bi_2O_3/CuBi_2O_4$/ITO, incubating same at a room temperature, performing rinsing with 0.1 M phosphate buffer solution (PBS) to remove unconjugated glutaraldehyde molecules, and obtaining GLD/$Bi_2O_3$/$CuBi_2O_4$/ITO;

performing drop coating on the GLD/$Bi_2O_3$/$CuBi_2O_4$/ITO with an AFB1 antigen solution with a certain concentration, incubating same at 4° C., and performing rinsing with the 0.1M PBS to obtain Ag/GLD/$Bi_2O_3$/$CuBi_2O_4$/ITO;

dropwise adding a 1% BSA solution onto the Ag/GLD/$Bi_2O_3$/$CuBi_2O_4$/ITO, incubating same at a room temperature, performing rinsing with the 0.1M PBS to obtain BSA/Ag/GLD/$Bi_2O_3$/$CuBi_2O_4$/ITO, so as to block out non-specific adsorption; and storing the constructed $Bi_2O_3/CuBi_2O_4$-based aflatoxin B1 biosensor in a refrigerator at 4° C. for later testing.

Preferably, a limit of detection of the photocathode $Bi_2O_3$/$CuBi_2O_4$ type PEC biosensor for detecting the AFB1 is 297.4 fg/mL, and a linear range is 1.4 pg/mL-280 ng/mL.

The present disclosure further provides an evaluation method for a PEC biosensor, including:

evaluating the effectiveness of the PEC biosensor by comparison with a high-performance liquid chromatography tandem mass spectrometry (HPLC-MS/MS) method by using artificial urine, lake water, peanut, and wheat samples;

displaying morphologies and structures of $Bi_2O_3$, $CuBi_2O_4$, and $Bi_2O_3/CuBi_2O_4$ using scanning electron microscope (SEM) images; and performing competitive immunoassay by using the PEC biosensor based on the $Bi_2O_3/CuBi_2O_4$ to determine whether the PEC biosensor is feasible for measuring the AFB1.

Preferably, crystal structures of $Bi_2O_3$, $CuBi_2O_4$, and $Bi_2O_3/CuBi_2O_4$ are measured using X-ray diffraction (XRD); and main lattices before and after the structural composition of the $Bi_2O_3/CuBi_2O_4$ are recorded according to XRD diffraction peaks of the $Bi_2O_3/CuBi_2O_4$, to evaluate a purification degree.

Preferably, an elemental composition and distribution of the $Bi_2O_3/CuBi_2O_4$ are observed by scanning a TEM-EDX to evaluate whether a $Bi_2O_3/CuBi_2O_4$ heterostructure is formed and whether Cu, Bi, and O elements are uniformly distributed in the morphology.

Preferably, optical properties of $Bi_2O_3$, $CuBi_2O_4$, and $Bi_2O_3/CuBi_2O_4$ are evaluated through an ultraviolet-visible diffuse reflection spectrum (UV-visDRS).

Preferably, measurement is performed by using a DMPO as a spin trapping agent through electron paramagnetic resonance (ESR) to detect presence of photoactive substances •$O^{2-}$ and OH of the PEC biosensor.

Beneficial effects: The construction method for the photocathode indirect competition sensor and the evaluaton method provided by the present disclosure. The construction method includes: synthesizing $Bi_2O_3/CuBi_2O_4$, $Bi_2O_3$, and $CuBi_2O_4$ using a high-temperature calcination method, uniformly dispersing $Bi_2O_3/CuBi_2O_4$ in a dispersion solution by ultrasound, and coating an electrode with droplets, naturally drying the electrode to obtain a $Bi_2O_3/CuBi_2O_4$/ITO-based sensing platform; performing treatment using a Perdew-Burke-Ernzerhof method with generalized gradient approximation; and constructing a $Bi_2O_3/CuBi_2O_4$-based biosensor. A limit of detection (LOD) of the photocathode $Bi_2O_3/CuBi_2O_4$ type PEC biosensor prepared in this solution for detecting the AFB1 is 297.4 fg/mL, and a linear range is 1.4 pg/mL-280 ng/mL. The photocathode $Bi_2O_3/CuBi_2O_4$ type PEC biosensor has good repeatability, reproducibility, stability, and specificity. In addition, for a validation purpose, a result of the PEC biosensor is compared with a result of an HPLC-MS/MS method in which AFB1 peanuts are added. The PEC biosensor constructed in the solution of the present disclosure has a broad application prospect in the fields of healthcare, environment, and food.

BRIEF DESCRIPTION OF THE DRAWINGS

FIG. 1 is a flowchart of a construction method for a photocathode indirect competition sensor provided in the present disclosure.

DETAILED DESCRIPTION OF THE EMBODIMENTS

Figure 2:
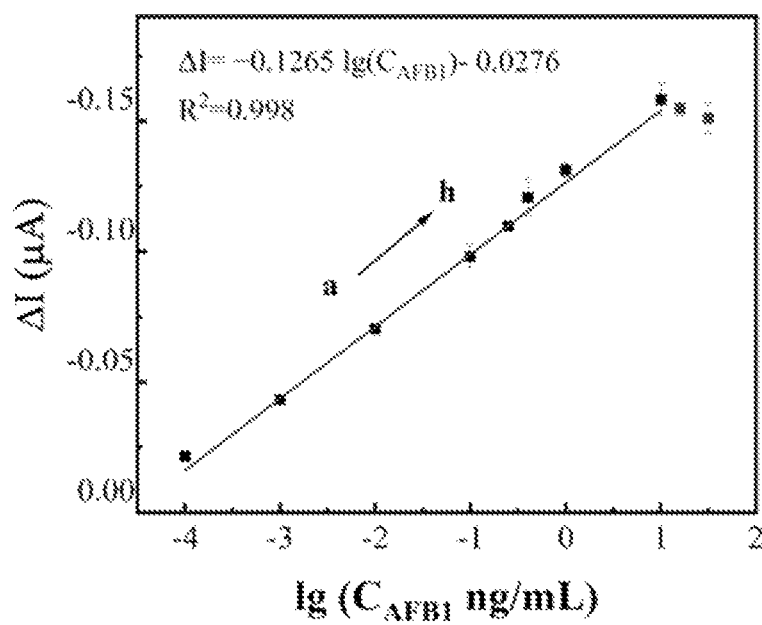
FIG. 2 is a curve diagram of responses of AFB1 at different concentrations in 0.1 M PBS to a PEC biosensor provided in the present disclosure.

The specific implementation modes of the present disclosure are further described below in detail in combination with the accompanying drawings and embodiments. The embodiments below are used to illustrate the present disclosure, but are not intended to limit the scope of the present disclosure.

FIG. 1 shows a construction method for a photocathode indirect competition sensor provided in the present disclosure, including: Z-type $Bi_2O_3/CuBi_2O_4$ was used as a sensing platform; a photoinduced electron Z-type transfer path and an energy band structure of $Bi_2O_3$ and $CuBi_2O_4$ were calculated using a DFT; and a $Bi_2O_3/CuBi_2O_4$-based aflatoxin B1 biosensor was constructed. An LOD of the photocathode $Bi_2O_3/CuBi_2O_4$ type PEC biosensor prepared in this solution for detecting the AFB1 was 297.4 fg/mL, and a linear range was 1.4 pg/mL-280 ng/mL. The photocathode $Bi_2O_3/CuBi_2O_4$ type PEC biosensor had good repeatability, reproducibility, stability, and specificity. In addition, for a validation purpose, a result of the PEC biosensor was compared with a result of an HPLC-MS/MS method in which AFB1 peanuts were added. The PEC biosensor constructed in the solution of the present disclosure has a broad application prospect in the fields of healthcare, environment, and food.

Specifically, the S1 includes: $Bi_2O_3/CuBi_2O_4$ was synthesized using a high-temperature calcination method. A specific process is as follows:

$Cu(NO_3)_2 \cdot 3H_2O$ (10-20 mM), $Bi(NO_3)_3 \cdot 5H_2O$ (10-50 mM), and glucose (10-70 mM) (1:1:7 to 1:5:7) were ground and uniformly mixed in quartz agate mortar. The above mixture was dried at 60° C. for several hours in a ceramic crucible to obtain an anhydrous precursor. The precursor was heated to 400° C. (at a temperature rise rate of 5° C./min), and the temperature was maintained in a tube furnace for 20-40 minutes. Obtained combustion residues were ground in the quartz agate mortar, and then calcined at the same heating rate at 500° C. for 2-6 hours in the ceramic crucible, to obtain $Bi_2O_3/CuBi_2O_4$. Monoclinal $Bi_2O_3$ and monoclinal $CuBi_2O_4$ were synthesized using the same method, but at a different molar ratio. The $Bi_2O_3/CuBi_2O_4$ was uniformly dispersed in a chitosan dispersion solution by ultrasound. 20 μL of the solution was dropwise applied onto ITO conductive glass, and the glass was naturally dried to obtain a $Bi_2O_3/CuBi_2O_4$/ITO-based sensing platform.

The S2 specifically includes: exchange correlation energy was treated using a Perdew-Burke-Ernzerhof method with generalized gradient approximation; and valence electron states of Bi, Cu, and O were studied by $5d^{10}6s^26p^3$, $3d^{10}4s^1$, and $2s^{22}p^4$, respectively. For the bulk $Bi_2O_3$ and the bulk $CuBi_2O_4$, their structures and electronic properties were calculated using cut-off energy of 520 eV and a 3×3×4 k-point mesh. For the $Bi_2O_3$ (001)/$CuBi_2O_4$ (100) heterostructure, the cut-off energy was 520 eV. k points were set for geometric optimization in 2×2×1, and a 4×4×1 mesh was used for electronic structure calculation. A vacuum space was set to be 20 Å to avoid periodic interactions. All the structures were loose until the maximum residual force on constituent atoms was less than 0.03 eV/Å. The vdW energy correction was described using a DFT-D2 empirical correction method.

The S3 specifically includes: the $Bi_2O_3/CuBi_2O_4$/ITO-based sensing platform was further modified, which includes the following steps: 5 μL of a glutaraldehyde aqueous solution was dipped onto $Bi_2O_3/CuBi_2O_4$/ITO and was incubated at a room temperature; rinsing was performed with 0.1 M PBS to remove unconjugated glutaraldehyde molecules, and GLD/$Bi_2O_3/CuBi_2O_4$/ITO was obtained; drop coating was performed on the GLD/$Bi_2O_3/CuBi_2O_4$/ITO with an AFB1 antigen solution with a certain concentration and was incubated at 4° C.; rinsing was performed with the 0.1M PBS to obtain Ag/GLD/Bi$_2$O$_3$/CuBi$_2$O$_4$/ITO; a 1% BSA (w/v) solution was dropwise added onto the Ag/GLD/Bi$_2$O$_3$/CuBi$_2$O$_4$/ITO and was incubated at a room temperature; rinsing was performed with the 0.1M PBS to obtain BSA/Ag/GLD/Bi$_2$O$_3$/CuBi$_2$O$_4$/ITO, so as to block out non-specific adsorption; and the constructed Bi$_2$O$_3$/CuBi$_2$O$_4$-based aflatoxin B1 biosensor was stored in a refrigerator at 4° C. for later testing.

In this example of the present discloses, the Z-type Bi$_2$O$_3$/CuBi$_2$O$_4$ was used as the sensing platform to immobilize monoclonal antigens to detect target molecules in healthcare, environments, and food. The photoinduced electron Z-type transfer path and the energy band structure of the Bi$_2$O$_3$ and the CuBi$_2$O$_4$ were calculated by using the DFT, and the energy band structure and a charge transfer process were calculated by using a VASP program and a projection enhanced wave method.

In addition, the Perdew-Burke-Ernzerhof method with the generalized gradient approximation was used to treat the exchange correlation energy. The valence electron states of Bi, Cu, and O were studied by 5d$^{10}$6s$^2$6p$^3$, 3d$^{10}$4s$^1$, and 2s$^2$2p$^4$, respectively. For the bulk Bi$_2$O$_3$ and the bulk CuBi$_2$O$_4$, their structures and electronic properties were calculated using cut-off energy of 520 eV and a 3×3×4 k-point mesh. For the Bi$_2$O$_3$ (001)/CuBi$_2$O$_4$ (100) heterostructure, the cut-off energy was 520 eV. k points were set for geometric optimization in 2×2×1, and a 4×4×1 mesh was used for electronic structure calculation. A vacuum space was set to be 20 Å to avoid periodic interactions. All the structures were loose until the maximum residual force on constituent atoms was less than 0.03 eV/Å.

The vdW energy correction was described using a DFT-D2 empirical correction method. Aflatoxin was selected as a model because it was listed as a Class I carcinogen by the International Agency for Research on Cancer, posing a huge threat to the ecological environment and human health.

The aflatoxin was selected as a typical small molecule, and an indirect competition immunoassay method was established. AFB1 was captured by an antibody mainly according to a specific antibody-antigen immunoreaction, and a few of remaining antibodies in a positive sample were recognized by an AFB1 antigen. The formation of Ab/BSA/Ag/GLD/Bi$_2$O$_3$/CuBi$_2$O$_4$/CS/ITO reduced photocurrent. If AFB1 was not present in a test sample, it indicated that AFB1 was completely captured by the AFB1 antigen. The minimum photocurrent was generated on BSA/Ag/GLD/Bi$_2$O$_3$/CuBi$_2$O$_4$/CS/ITO in conjunction with Ab. Photocurrent changes between Ab/BSA/Ag/GLD/Bi$_2$O$_3$/CuBi$_2$O$_4$/CS/ITO (excluding AFB1) and BSA/Ag/GLD/Bi$_2$O$_3$/CuBi$_2$O$_4$/CS/ITO (including AFB1) were recorded using an ammeter, and working curve calibration were performed.

Results indicate that the Bi$_2$O$_3$/CuBi$_2$O$_4$-based PEC biosensor is feasible for measuring the AFB1. The photocurrent response of the Bi$_2$O$_3$/CuBi$_2$O$_4$ is improved by enhancing the visible light absorption capacity, enhancing the separation efficiency of e$^-$/h$^+$, and increasing the charge transfer rate.

Under optimized conditions, an LOD, linear range, recovery rate, repeatability, reproducibility, stability, and interference resistance of the Bi$_2$O$_3$/CuBi$_2$O$_4$-based PEC biosensor are studied. FIG.2 shows a curve of responses of AFB1 at different concentrations in the 0.1 M PBS to the PEC biosensor.

The effectiveness of the Bi$_2$O$_3$/CuBi$_2$O$_4$-based PEC biosensor was verified by comparison with an HPLC-MS/MS method by using artificial urine, lake water, peanut, and wheat samples, so as to demonstrate the widespread application of the Bi$_2$O$_3$/CuBi$_2$O$_4$-based PEC biosensor in the fields of healthcare, environment, and food.

A crystal structure, elemental composition, state, and morphology of a Bi$_2$O$_3$/CuBi$_2$O$_4$ heterostructure were characterized.

Crystal structures of Bi$_2$O$_3$, CuBi$_2$O$_4$ and Bi$_2$O$_3$/CuBi$_2$O$_4$ were measured using XRD. Diffraction peaks of Bi$_2$O$_3$ and CuBi$_2$O$_4$ well matched diffraction peaks of a monoclinic phase Bi$_2$O$_3$ (JCPDS No. 71-2274) and a tetragonal phase CuBi$_2$O$_4$ (JCPDS No. 71-1774) respectively. Crystal faces (−121) (−202) (041) and (−104) of the monoclinic Bi$_2$O$_3$ were diffraction peaks of 27.39°, 33.26°, 46.33°, and 48.59° respectively. The tetragonal CuBi2O4 had obvious diffraction peaks on crystal faces (130), (141), (402), (332), and (413), which were mainly concentrated at values of 2θ of 33.37°, 46.00°, 53.02°, 55.75°, and 66.19°. Main lattices before and after the structural composition of the Bi$_2$O$_3$/CuBi$_2$O$_4$ tetragonal structure were recorded according to the XRD diffraction peaks of the Bi$_2$O$_3$/CuBi$_2$O$_4$, indicating that the degree of purification was high.

An X-ray photoelectron spectroscopy (XPS) scanning spectrum scan spectrum showed C, Cu, Bi, and O. External C 1s peak was used for calibration. It was found through analysis that the four main peaks of CuBi$_2$O$_4$ at 934.6 eV, 942.9 eV, 954.7 eV and 962.8 eV can be attributed to 2p1/2 (954.7 eV) and 2p3/2 (934.6 eV), and the two satellite peaks at 942.9 eV and 962.8 eV can be attributed to a Cu$^{2+}$ oxidation state. A Bi 4f spectrum contained two peaks that can be attributed to Bi 4f5/2 (164.9 eV) and Bi 4f7/2 (159.6 eV), indicating that Bi was in a +3 oxidation state. O 1s spectrum contained two peaks that can be attributed to a surface adsorption group (O$_\beta$) (532.1 eV) and lattice oxygen (O$_\alpha$) (530.6 eV).

The morphologies and structures of Bi$_2$O$_3$, CuBi$_2$O$_4$, and Bi$_2$O$_3$/CuBi$_2$O$_4$ were displayed using SEM images. Analysis results indicate that Bi$_2$O$_3$ has an irregular porous structure, while CuBi$_2$O$_4$ is an irregular sphere with an average diameter of approximately 100-200 nm. In order to provide a more detailed description of the microstructure of Bi$_2$O$_3$/CuBi$_2$O$_4$, analysis was performed using a transmission electron microscope (TEM) and high-power TEM (HR-TEM), and it was found that Bi$_2$O$_3$/CuBi$_2$O$_4$ has a combination of spherical and porous structures. In Bi$_2$O$_3$/CuBi$_2$O$_4$, a lattice spacing of Bi$_2$O$_3$ on the crystal face of 0.32 nm (−121) and lattice fringes of CuBi$_2$O$_4$ on the crystal face of 0.26 nm (130) were clearly recorded, and were consistent with XRD results. By scanning TEM (STEM)-EDX mapping, the elemental composition and distribution of Bi$_2$O$_3$/CuBi$_2$O$_4$ were observed, indicating that Bi$_2$O$_3$ was successfully assembled on a surface of CuBi$_2$O$_4$ to form a Bi$_2$O$_3$/CuBi$_2$O$_4$ heterostructure, with Cu, Bi, and O elements uniformly distributed in the morphology.

The energy band structure measurement and charge transfer mechanism of Bi$_2$O$_3$/CuBi$_2$O$_4$ was as follows: The optical properties of Bi$_2$O$_3$, CuBi$_2$O$_4$ and Bi$_2$O$_3$/CuBi$_2$O$_4$ were evaluated by an ultraviolet-visible diffuse reflection spectrum (DRS). The absorption of Bi$_2$O$_3$ at 463 nm proved that Bi$_2$O$_3$ can absorb visible light and CuBi$_2$O$_4$ can absorb near-infrared light. Compared with Bi$_2$O$_3$, Bi$_2$O$_3$/CuBi$_2$O$_4$ has higher broad absorption and visible light absorption intensity. The band gap energy (E$_g$) was calculated as follows αhv=A(hv−E$_g$)n/2, where α, h, v, A, and n represented an absorption index, a Planck constant, an incident light frequency, and an optical transition type, respectively. The energy bands of Bi$_2$O$_3$ and CuBi$_2$O$_4$ were 2.66 eV and 1.58 eV, respectively, consistent with previous reported results.

Calculation formulas of a valence band potential ($E_{VB}$) and a conduction band potential ($E_{CB}$) of $Bi_2O_3$ and $CuBi_2O_4$ were as follows:

$$E_{CB}=X-E_e-\tfrac{1}{2}E_g \quad (2)$$

$$E_{VB}=E_{CB}+E_g \quad (3)$$

where $E_e$ and X were free electron energy and electronegativity of a semiconductor respectively. Band energy levels of $CuBi_2O_4$ ($E_{CB}=-0.54$ eV, $E_{VB}=1.04$ eV) and $Bi_2O_3$ ($E_{CB}=0.28$ eV, $E_{VB}=2.94$ eV) were obtained.

Measurement was performed by using a DMPO as a spin trapping agent through ESR to detect presence of photoactive substances $\cdot O^{2-}$ and $\cdot OH$. Under a dark condition, no feature signals were recorded in an ESR spectrum. Signals of $\cdot O^{2-}$ and $\cdot OH$ radicals were found under the action of the visible light, and changes in $DMPO^-\cdot O^{2-}$ and $DMPO^-\cdot OH$ signals indicated that main active oxygen in a Z-type $Bi_2O_3/CuBi_2O_4$ photocatalyst were $\cdot O^{2-}$ and $\cdot OH$.

The calculation of CB, VB, and ESR experimental results indicated that photo-induced charges were transferred through a Z-type mechanism. Under the action of the visible light, $e^-$ generated on CB of $Bi_2O_3$ was recombined with $h^+$ generated on VB of $CuBi_2O_4$ through electrostatic interaction. At the same time, $e^-$ with high reducing property was retained in CB of $CuBi_2O_4$, and $h^+$ with high oxidizability was retained in VB of $Bi_2O_3$, to complete a redox reaction. This Z-type heterojunction facilitates effective spatial separation of $e^-/h^+$ and increases an upper limit of the redox capacity. CB of $CuBi_2O_4$ is $-0.54$ eV, which is higher than a standard oxidation potential of $O_2/\cdot O^{2-}$ ($-0.33$ eV), and $e^-$ in $CuBi_2O_4$ can reduce $O_2$ to generate $\cdot O^{2-}$. VB of $Bi_2O_3$ is 2.94 eV, which was higher than the standard redox potential of $OH^-/\cdot OH$ (2.4 eV), indicating that $h^+$ can oxidize $H_2O/OH^-$ to generate $\cdot OH$.

The $Bi_2O_3/CuBi_2O_4$-based PEC biosensor was used to perform competitive immunoassay. AFB1 was captured by an antibody mainly according to a specific antibody-antigen immunoreaction, and a few of remaining antibodies in a positive sample were recognized by an AFB 1 antigen. The formation of $Ab/BSA/Ag/GLD/Bi_2O_3/CuBi_2O_4/CS/ITO$ reduced photocurrent. If AFB1 was not present in a test sample, AFB1 was completely captured by the AFB1 antigen. The minimum photocurrent was generated on $BSA/Ag/GLD/Bi_2O_3/CuBi_2O_4/CS/ITO$ in conjunction with Ab. Photocurrent changes between $Ab/BSA/Ag/GLD/Bi_2O_3/CuBi_2O_4/CS/ITO$ (excluding AFB1) and $BSA/Ag/GLD/Bi_2O_3/CuBi_2O_4/CS/ITO$ (including AFB1) were recorded using an ammeter, and working curve calibration were performed. Results indicate that the $Bi_2O_3/CuBi_2O_4$-based PEC biosensor is feasible for measuring the AFB1.

Interfacial charge transferring and step-by-step assembling processes of the $Bi_2O_3/CuBi_2O_4$-based PEC biosensor were studied through an electron transmission electron microscope (EIS) and a photocurrent-time test. An impedance spectrum was composed of a semicircle and a linear portion. The semicircle indicated that the electron transfer resistance increased with an increase of a diameter of the semicircle. The linear portion represented a diffusion step. A diameter order of five semicircles was $Bi_2O_3/CuBi_2O_4 < GLD/Bi_2O_3/CuBi_2O_4 < Ag/GLD/Bi_2O_3/CuBi_2O_4 < BSA/Ag/GLD/Bi_2O_3/CuBi_2O_4 < Ab/BSA/Ag/GLD/Bi_2O_3/CuBi_2O_4$. Since an immune complex hindered electron transfer of a redox probe, the diameter of the semicircle gradually increased, indicating that the $Bi_2O_3/CuBi_2O_4$ modified electrode was successfully immobilized.

An impedance spectrum was composed of a semicircle and a linear portion. The linear portion normally represented a diffusion step size. The semicircle (the electron transfer resistance $R_{et}$) represented the electron transfer resistance. $R_{et}$ increased with the increase of the diameter of the semicircle. A smaller $R_{et}$ represented a higher charge transfer rate. During the preparation of the PEC biosensor, changes in $R_{et}$ indicated a transition in interfacial properties in the step-by-step assembling process. The minimum $R_{et}$ value of $Bi_2O_3/CuBi_2O_4/ITO$ indicated that $Bi_2O_3/CuBi_2O_4/ITO$ has optimal conductivity, while Ret increased after GLD modification on $Bi_2O_3/CuBi_2O_4/ITO$. If an aflatoxin antigen, BSA, and Ab were loaded onto $GLD/Bi_2O_3/CuBi_2O_4/ITO$, the diameter of the semicircle gradually increased, namely, $R_{et}$ increased, due to the obstruction of the immune complex to the redox probe, indicating its successful immobilization on the $Bi_2O_3/CuBi_2O_4$ modified electrode.

Photocurrent-time test was performed in the PBS to confirm successful layer-by-layer modification of the electrode. The photocurrent of the $Bi_2O_3/CuBi_2O_4$ electrode was the highest, which was $-0.39$ µA, indicating that the electrode had good photoactive matrix properties. An additional GLD electrode caused a decrease of $-0.32$ µA in the photocurrent. Subsequently, through continuous modification by the antigen, the cathode photocurrent was continuously reduced, and the antigen and BSA hindered the reduction of an $O_2$ electron acceptor. If there was a small amount of AFB1 in the test sample, the stereospecific blockade of AbAFB1 would lead to a decrease in the photocurrent. During the gradual modification of the PEC electrode, changes in photocurrent values indicated successful development of the $Bi_2O_3/CuBi_2O_4$-based PEC biosensor.

10 ng/mL of AFB1 was applied to optimize the concentrations, incubation time, and application potentials of the AFB1 antigen and antibody. For the concentration of the AFB1 antigen, as the concentration of the AFB1 antigen increased to 20 ng/mL, the cathode photocurrent gradually weakened. Therefore, according to the competitive immune response of Ab to capturing the AFB1 antigen on the PEC electrode or in the sample, 20 ng/mL of the AFB1 antigen was selected as an incubation concentration. The concentration of Ab was another factor that affects the performance of the PEC biosensor. Results showed that as the concentration of Ab increased from 5 ng/mL to 15 ng/mL, the photocurrent decreased.

Therefore, 15 ng/mL of Ab was used in the following experiment. The photocurrent response of the $Bi_2O_3/CuBi_2O_4$ electrode increased as the incubation time was prolonged to 50 minutes. A high bias voltage would have a negative impact on the AFB1 antigen and biosensing on the $Bi_2O_3/CuBi_2O_4$ photoelectrode. A low applied potential was beneficial for eliminating interference from complex matrices in actual samples. As the potential increased from $-0.3$ V to $+0.1$ V, a photocurrent value increased from $-0.1896$ µA to $-0.1898$ µA and then decreased to $-0.0078$ µA, thereby obtaining the optimal configuration voltage of $-0.2$ V.

The analytical performance of the $Bi_2O_3/CuBi_2O_4$-based PEC biosensor was evaluated by performing a time-varying photocurrent response test using AFB1. In terms of linearity, the detection concentration of AFB1 ranged from 1.4 pg/mL to 280 ng/mL, as shown in FIG. 2. A linear fitting equation was $\Delta I=-0.1265 \lg C_{(AFB1)}-0.0276$, $R2=0.998$, $n=3$. $\Delta I$ was a variation of the cathode photocurrent. The LOD of 21 blank samples was 297.4 fg/mL. Compared with previous reports, the $Bi_2O_3/CuBi_2O_4$-based PEC biosensor had a lower LOD of up to 34 times for AFB1. In addition, a wider linear range (8 orders of magnitude) was also recorded, as shown in Table 1:

TABLE 1

Comparison of AFB1 detection results in different methods

| Method | Matrix | | | Linear range (ng/ml) | LOD (pg/ml) | References |
|---|---|---|---|---|---|---|
| | Health-care | Environment | Food | | | |
| Electro-chemical luminescence sensing | / | / | Lotus seeds | 0.05-100 | 10.00 | Sun et al. 2020 |
| Electro-chemical luminescence sensing | / | / | Rice, wheat, and corn | 0.1-100 | 33.00 | Xiong et al. 2019 |
| Fluorescent sensing | / | / | Corn, peanut | 0-375 | 10.00 | Fan et al. 2021 |
| Electro-chemical sensing | / | / | Beer, wheat | 0.125-16 | 120.0 | Goud et al. 2016 |
| Electro-chemical sensing | / | / | Wheat | 0.01-100 | 3.300 | Pan et al. 2018 |
| Photo-electro-chemistry immuno-sense | Urine | Lake water | Peanut | 0.0014-280 | 0.297 | This study |

These results all showed that the $Bi_2O_3/CuBi_2O_4$ PEC biosensor meets the requirement for fast and sensitive detection of AFB1.

The repeatability, reproducibility, stability, and specificity of the $Bi_2O_3/CuBi_2O_4$ PEC biosensor were further evaluated through a labeling experiment. One $Bi_2O_3/CuBi_2O_4$-based PEC biosensor was tested for six times for AFB1 1.0 ng/mL, which showed a relative standard deviation (RSD) of 1.17%, while for its reproducibility, six parallel photoelectric biosensors were tested for AFB1 1.0 ng/mL, and an experimental result showed that an RSD was 3.12%. One PEC biosensor was subjected to 15 cycles of light/dark reactions with 1.0 ng/mL AFB1 to detect its stability. It was found that there was little change in photocurrent. For its specificity, $T_2$, DON, FBI, OTA, and ZEN (each of which was 5.0 ng/mL) were used as typical interference detection AFB1 (1.0 ng/mL). Results indicated that a measurement signal deviation of the $Bi_2O_3/CuBi_2O_4$-based PEC biosensor on AFB1 was less than 9.24%. The above results indicated that the $Bi_2O_3/CuBi_2O_4$-based PEC biosensor had excellent repeatability, reproducibility, stability, and specificity, and had an excellent prospect in AFB1 detection.

In order to determine the practicability of the $Bi_2O_3/CuBi_2O_4$ PEC biosensor, artificial urine, lake water, and peanuts were selected as real samples. Before the labeling experiment, absence of AFB1 in these samples was confirmed using the HPLC-MS/MS method. Since AFB1 (0, 0.1, and 50 ng/mL) in the actual samples was labeled, results of the $Bi_2O_3/CuBi_2O_4$-based PEC biosensor were highly consistent with those obtained by the HPLC-MS/MS method, and the recovery rate ranged from 93% to 112%. Therefore, the $Bi_2O_3/CuBi_2O_4$-based PEC biosensor can be widely applied in fields such as healthcare, environment, and food.

In order to cope with the challenges of the interference capacity and the sensitivity, the $Bi_2O_3/CuBi_2O_4$ type PEC sensor improves the cathode photocurrent by providing good visible light utilization rate, conductivity, and charge separation efficiency and promoting effective separation of electron-hole pairs, thus improving the sensitivity of PEC. As a proof of concept, $Bi_2O_3/CuBi_2O_4$ was synthesized in one step and characterized. DFT results showed that the photoinduced electron transfer path of $Bi_2O_3/CuBi_2O_4$ is a Z-type heterojunction model, which greatly matched ESR experimental results. The energy band structure and total density of state (DOS) of $Bi_2O_3$ and $CuBi_2O_4$ were used to simulate the energy band structure of $Bi_2O_3$ and $CuBi_2O_4$. According to the energy band structure of $Bi_2O_3$ and $CuBi_2O4$, calculation results showed that $Bi_2O_3$ and $CuBi_2O_4$ were both indirect semiconductors with band gaps of 2.46 eV and 1.52 eV, respectively. The calculation results were consistent with the energy band experimental results of $Bi_2O_3$ and $CuBi_2O_4$.

DOSs of the energy band structure and interfacial electronic structure of $Bi_2O_3$ and $CuBi_2O_4$ were studied. CB at the bottom of $Bi_2O_3$ was occupied by the Bi 6p state. The VB top was a hybrid of Bi 6p and 0 2p. The CB bottom was mainly composed of Bi 6p and Cu 4s, while VB contained O 2p mixed with Bi 6p. Band gaps in the $Bi_2O_3/CuBi_2O_4$ heterojunction are staggered. In order to explore the Z-type charge transfer process at a $Bi_2O_3/CuBi_2O_4$ interface, differential charge density analysis of $Bi_2O_3/CuBi_2O_4$ was carried out. Results indicated that there was a charge distribution at the $Bi_2O_3/CuBi_2O_4$ heterojunction interface. On the contrary, changes observed beyond the interface were minimal. A differential charge density of the $Bi_2O_3/CuBi_2O_4$ heterojunction showed that holes at $CuBi_2O_4$ VB were combined with excited state electrons of $Bi_2O_3$. The above charge transfer generated an internal electric field in the $Bi_2O_3/CuBi_2O_4$ heterostructure, which further accelerated the separation of $e^-/h^+$. The efficient interfacial electron transfer mechanism based on the Z-type heterostructure can greatly improve the separation performance of $e^-/h^+$, thereby improving the sensitivity of the PEC biosensor.

The Z-type charge transfer mode of $Bi_2O_3/CuBi_2O_4$ significantly improves the catalytic efficiency by increasing accumulation of photoinduced electrons, allowing more photoinduced electrons to participate in a reduction reaction. A $Bi_2O_3/CuBi_2O_4$-based PEC biosensor was constructed to detect harmful AFB1 in healthcare, environment, and food. Under optimized conditions, the LOD of the $Bi_2O_3/CuBi_2O_4$-based PEC biosensor was 297.4 fg/mL, and the linear range was 1.4 pg/mL-280 ng/mL. In the labeling experiment, the PEC biosensor had good repeatability, reproducibility, stability, and specificity. For verification, AFB1 was detected by using lake water, peanuts, and artificial urine as substrates, with a recovery rate of 93-112%. The detection results of the $Bi2O_3/CuBi_2O_4$-based PEC biosensor were consistent with those of the HPLC-MS/MS method. The $Bi_2O_3/CuBi_2O_4$-based PEC biosensor can be widely used to detect mycotoxin in healthcare, environment, and food.

It should be noted that in the above-mentioned embodiments, the descriptions of all the embodiments have their own focuses. For parts that are not described in detail in an embodiment, reference may be made to related descriptions of other embodiments.

Obviously, those skilled in the art can make various changes and modifications to the present invention without departing from the spirit and scope of the present invention. Therefore, if these changes and transformations of the present disclosure fall within the scope of the claims of the present disclosure and equivalent technologies of the present disclosure, the present disclosure is intended to include these changes and transformations.

What is claimed is:

1. A construction method for a photocathode indirect competition sensor, comprising the following steps:
S1), synthesizing $Bi_2O_3/CuBi_2O_4$, using a high-temperature calcination method, uniformly dispersing $Bi_2O_3/CuBi_2O_4$ in a dispersion solution by ultrasound, and drop coating Indium Tin Oxide (ITO) conductive glass, and drying the ITO conductive glass to obtain a $Bi_2O_3/CuBi_2O_4$/ITO-based sensing platform;
wherein S1) comprises:
grinding $Cu(NO_3)_2 \cdot 3H_2O$, $Bi(NO_3)_3 \cdot 5H_2O$, and glucose at a molar ratio of 1:1:7 to 1:5:7 in a quartz agate mortar for 5-10 minutes to obtain a mixture;
drying the mixture at 60° C. in a ceramic crucible to obtain an anhydrous precursor of $Bi_2O_3/CuBi_2O_4$;
heating the anhydrous precursor to 400° C., and maintaining the temperature in a tube furnace for 20-40 minutes to obtain combustion residues; and
grinding the combustion residues in the quartz agate mortar, then calcining at 500° C. for 2-6 hours in the ceramic crucible, and finally obtaining $Bi_2O_3/CuBi_2O_4$; and
S2), obtaining the photocathode indirect competition sensor based on the $Bi_2O_3/CuBi_2O_4$/ITO-based sensing platform;
wherein the S2) specifically comprises:
dripping 3-10 μL of glutaraldehyde (GLD) aqueous solution onto the $Bi_2O_3/CuBi_2O_4$/ITO-based sensing platform, incubating at a room temperature for 30-60 minutes, performing rinsing with 0.1 M phosphate buffer solution (PBS) to remove unconjugated glutaraldehyde molecules, and obtaining $GLD/Bi_2O_3/CuBi_2O_4$/ITO;
performing drop coating on the $GLD/Bi_2O_3/CuBi_2O_4$/ITO with a target antigen solution with a predefined concentration, incubating at 4° C., and performing rinsing with the 0.1 M PBS to obtain $Ag/GLD/Bi_2O_3/CuBi_2O_4$/ITO;
dropwise adding a 1% bovine serum albumin (BSA) solution onto the $Ag/GLD/Bi_2O_3/CuBi_2O_4$/ITO, incubating at a room temperature, performing rinsing with the 0.1 M PBS to obtain $BSA/Ag/GLD/Bi_2O_3/CuBi_2O_4$/ITO as the photocathode indirect competition sensor.

2. An evaluation method for evaluating the performance of the photocathode indirect competition sensor according to claim 1, comprising:
evaluating the effectiveness of the photocathode indirect competition sensor in measuring aflatoxin (AF) B1 by comparison with a high-performance liquid chromatography chromatography-tandem mass spectrometry method with artificial urine, lake water, peanut, and wheat samples;
performing analysis of morphologies and structures of $Bi_2O_3$, $CuBi_2O_4$, and $Bi_2O_3/CuBi_2O_4$ using scanning electron microscope images; and
performing competitive immunoassay with the photocathode indirect competition sensor to determine whether the photocathode indirect competition sensor is effective for measuring the AFB1 in the samples.

3. The evaluation method according to claim 2, further comprises:
measuring crystal structures of $Bi_2O_3$, $CuBi_2O_4$, and $Bi_2O_3/CuBi_2O_4$ using X-ray diffraction (XRD); and
performing analysis of purity degree according to XRD diffraction peaks of the $Bi_2O_3/CuBi_2O_4$.

4. The evaluation method according to claim 2, further comprises: performing a transmission electron microscopy-energy dispersive X-ray spectroscopy (TEM-EDX) analysis to evaluate whether a $Bi_2O_3/CuBi_2O_4$ heterostructure is formed and whether Cu, Bi, and O elements are uniformly distributed in the morphology.

5. The evaluation method according to claim 2, further comprises: performing optical property measurements via an ultraviolet-visible diffuse reflection spectrum (UV-vis-DRS) to evaluate the optical properties of $Bi_2O_3$, $CuBi_2O_4$, and $Bi_2O_3/CuBi_2O_4$.

6. The evaluation method according to claim 2, further comprises: measuring by using 5,5-dimethyl-1-pyrroline-noxide (DMPO) as a spin trapping agent through electron paramagnetic resonance (ESR) to detect the presence of photoactive substances •$O^{2-}$ and •OH in the photocathode indirect competition sensor.

* * * * *